US009907692B2

United States Patent

(12) United States Patent
Binversie et al.

(10) Patent No.: US 9,907,692 B2
(45) Date of Patent: Mar. 6, 2018

(54) THERAPEUTIC THERMAL COMPRESSION DEVICE

(71) Applicant: ZENITH TECHNICAL INNOVATIONS, LLC, Waukegan, IL (US)

(72) Inventors: Gregory Binversie, Grayslake, IL (US); William Sultan, Waukegan, IL (US); William Corwin, Beach Park, IL (US); John Bucher, Wadsworth, IL (US)

(73) Assignee: ZENITH TECHNICAL INNOVATIONS, LLC, Gurnee, IL (US)

( * ) Notice: Subject to any disclaimer, the term of this patent is extended or adjusted under 35 U.S.C. 154(b) by 466 days.

(21) Appl. No.: 14/559,452

(22) Filed: Dec. 3, 2014

(65) Prior Publication Data

US 2015/0182375 A1 Jul. 2, 2015

Related U.S. Application Data

(60) Provisional application No. 61/921,749, filed on Dec. 30, 2013.

(51) Int. Cl.
*A61F 7/00* (2006.01)
*A61N 1/04* (2006.01)
(Continued)

(52) U.S. Cl.
CPC ............ *A61F 7/007* (2013.01); *A61N 1/0456* (2013.01); *A61B 5/4836* (2013.01); *A61B 5/6804* (2013.01);
(Continued)

(58) Field of Classification Search
CPC .............. A61F 7/007; A61F 2007/0295; A61F 2007/0096; A61F 2007/0075; A61N 1/0456; A61B 5/4836; A61B 5/6804; A61H 2201/5046; A61H 2201/1614; A61H 9/0078; A61H 2201/0207; A61H 2201/0214; A61H 2201/0285; A61H 2201/10; A61H 2201/1604; A61H 2201/1609; A61H 2201/1619;
(Continued)

(56) References Cited

U.S. PATENT DOCUMENTS 4,640,284 A * 2/1987 Ruderian ................ A61F 7/007 126/204
5,800,490 A 9/1998 Patz et al.
(Continued)

OTHER PUBLICATIONS

PulsarScientific®, Recovery+ Features and Specifications webpage, pulsarscientific.com/products/recovery, retrieved Nov. 20, 2014.

*Primary Examiner* — Steven Douglas
(74) *Attorney, Agent, or Firm* — Ryan Kromholz & Manion, S.C.

(57) ABSTRACT

Systems and methods directed to the art of therapeutic thermal compression are provided. A therapeutic device capable of providing various therapeutic stimuli, including thermal energy transfer and applied pressure. The therapeutic device has a heating/cooling system, a temperature moderating system, a compression system, and a control system which controls the amount of pressure applied, the degree of temperature applied, and the duration of each application of therapeutic stimuli.

2 Claims, 8 Drawing Sheets

30 32 322 324 318 34 320 310 40 410 222 210

(51) Int. Cl.
*A61F 7/02* (2006.01)
*A61H 9/00* (2006.01)
*A61B 5/00* (2006.01)

(52) U.S. Cl.
CPC ................ *A61F 2007/0075* (2013.01); *A61F 2007/0096* (2013.01); *A61F 2007/0295* (2013.01); *A61H 9/0078* (2013.01); *A61H 2201/0207* (2013.01); *A61H 2201/0214* (2013.01); *A61H 2201/0285* (2013.01); *A61H 2201/10* (2013.01); *A61H 2201/164* (2013.01); *A61H 2201/1604* (2013.01); *A61H 2201/1609* (2013.01); *A61H 2201/1614* (2013.01); *A61H 2201/1619* (2013.01); *A61H 2201/1623* (2013.01); *A61H 2201/1635* (2013.01); *A61H 2201/5043* (2013.01); *A61H 2201/5046* (2013.01)

(58) Field of Classification Search
CPC .... A61H 2201/1623; A61H 2201/1635; A61H 2201/164; A61H 2201/5043
See application file for complete search history.

(56) References Cited

U.S. PATENT DOCUMENTS

| | | | | |
|---|---|---|---|---|
| 6,023,932 | A * | 2/2000 | Johnston | A61F 7/007 607/96 |
| 6,125,636 | A * | 10/2000 | Taylor | A61F 7/10 62/259.3 |
| 6,345,507 | B1 | 2/2002 | Gillen | |
| 6,375,674 | B1 | 4/2002 | Carson | |
| 6,679,908 | B2 * | 1/2004 | Shimizu | A61F 7/02 607/109 |
| 7,243,509 | B2 | 7/2007 | Trinh et al. | |
| 8,397,518 | B1 | 3/2013 | Vistakula | |
| 2005/0143797 | A1 * | 6/2005 | Parish | A61F 5/34 607/104 |
| 2008/0058911 | A1 * | 3/2008 | Parish | A61F 7/0085 607/104 |
| 2008/0188915 | A1 * | 8/2008 | Mills | A61F 7/007 607/112 |
| 2013/0238043 | A1 | 9/2013 | Beardall et al. | |

* cited by examiner 300
322
320
302
312
314
318
30
324
310
304
316

30
7B
7B
318
314
316
312
10
40

400
30

414
410
30
9B
9B
410
414
10
412
40
414

THERAPEUTIC THERMAL COMPRESSION DEVICE

RELATED APPLICATIONS

This application claims the benefit of U.S. Provisional Patent Application Ser. No. 61/921,749, entitled "Therapeutic Thermal Compression Device," filed 30 Dec. 2013.

BACKGROUND OF THE INVENTION

The present invention is directed towards devices and methods for the treatment of medical conditions, particularly where cryotherapy or heat are recommended.

Acute sports injuries and post joint surgery is accompanied by pain and swelling. Most often the professional practitioner provides both therapeutic and analgesic modalities to treat these symptoms. The most common treatment to reduce both pain and swelling is to apply cold in the form of ice or circulating cooled water.

Ice bags are the most commonly used modality for treating acute injuries like severe strains, sprains, contusions, and concussions. There are commercial products that provide circulating cool water through wraps designed for different body parts, but these products have limited ability to control the treatment. Many commercial products are not portable and are too expensive to send home with a patient. For acute injuries the patient is most often sent home with ice bags for the remainder of the treatment.

There are many devices on the market for managing thermal treatment regiments including electric blankets, circulating cooled and heated water in blankets, pads & body part shaped garments, chemical and inert products bagged for the freezer and microwave, along with the old standby hot water bottles and ice bags.

The electric heating devices have wires channeled in fabric or flexible plastic that produce a resistance and resulting heat that is controlled by a rheostat in increase and decrease the input current.

There are sophisticated and more costly devices that are used by hospitals, and surgical care physicians. Some of the more sophisticated devices use controllers to operate refrigerating units with condensers, evaporators, and compressors to cool the circulating water and heating elements to create warm fluids. Both the cooled and warmed fluids require a pumping system to circulate the fluids through the tubing in the pad, blanket, garment or fixture used to provide the thermal treatment.

Peltier devices known as Thermoelectric coolers/modules (TEC/TEM) have been on the market for a number of years, but have been applied to industrial cooling applications and small coolers for the most part. In the late 1980's TEM's found their way into the medical device industry. Most of the applications have been for creating cooling or heating fluids for circulation through a fitted "garment", pad or blanket for thermal treatment of injuries or post-surgery. These devices were aimed at replacing the refrigerant and heating element technology. The TEM technology eliminated the refrigeration and heating element, but still required the fluid reservoir and pumping system. These units have temperature sensors to control the temperature, but with a large mass of fluid to control, the unit can have significant temperature fluctuation. The temperature is controlled by alternating the polarity of the current to the TEM based on the temperature sensor's reading. Due to the volume of fluid needed to reach temperature and the potential for heat exchanged (loss or gain) through the insulated garment, it takes significant time for the fluid in the reservoir to reach and maintain the desired temperature.

Additionally, a larger TEM and more energy is required than with direct TEM treatment to the targeted area through a thermal conductive substrate placed directly on area of treatment.

The circulating fluid cannot penetrate the treatment site as quickly nor reach the critical temperature as rapidly. If temperatures of less than 35° F. need to be achieved, the circulating fluid system would not work. Circulating systems are not able to alter the speed of increase or decrease in temperature as rapidly as direct treatment.

Current direct TEM treatment devices have overcome many of the issues related to fluid, but do not achieve some of the issues related to thermal treatment. One of the issues is ensuring that treatment is carried out as prescribed by the professional recommending treatment.

For acute injuries, e.g., strains, sprains, minor tears, trainers and other professionals recommend 15 to 30 minutes of ice treatment followed by 30 to 45 minutes off continuously during waking hours for the first 24 to 72 hours depending on the severity and improvement speed of the patient. Very few patients maintain consistency in the process simply because it is not practical.

With the advent and continued advancements of solid state circuitry and improved microprocessors, controllers can be miniaturized and still managing many actions. With apps for handheld devices, and wireless capabilities, we now can communicate in ways that were not available just a few years ago.

New thermal treatment devices can now use these technologies to ensure that recommended treatment is completed as recommended and that actual results and use can be maintained and recorded for review and corrective action. Ensured treatment may lead to shortened recovery.

Additionally, improved thermal qualities of the substrate used to remove or transmit heat from the site, will have a significant impact on speed of penetration and control of the temperature of the thermal device.

SUMMARY OF THE INVENTION

This medical device relates to providing both analgesic and therapeutic treatment for acute injuries, post-surgery, and medical conditions, e.g., arthritis, migraines, and other illnesses where cryotherapy or heat are recommended. The device provides treatment through various temperature and compression applications along with optional treatments of TENS and massage.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
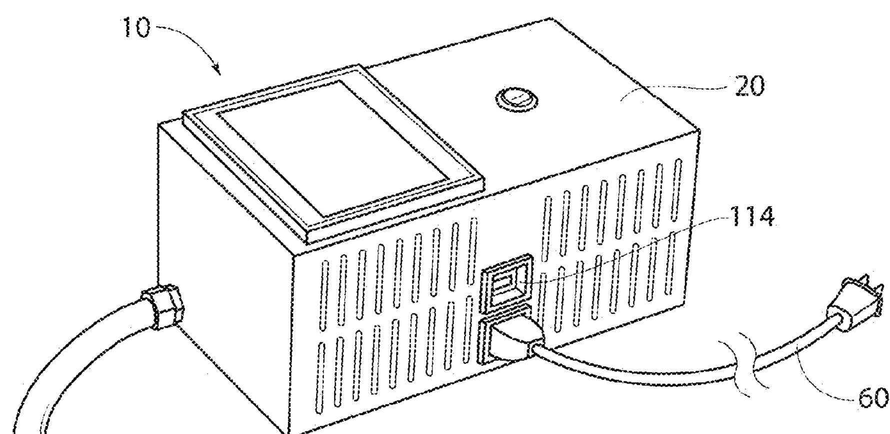
FIG. 1 is a perspective view of a treatment system according to the present invention.
Figure 1:
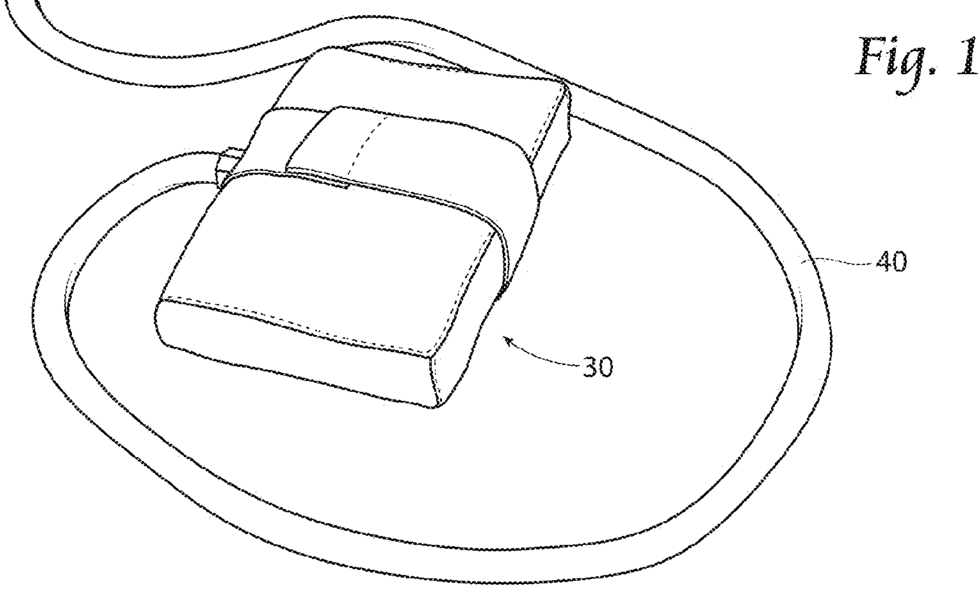

Now turning to the figures, FIG. 1 illustrates a therapeutic device 10 according to the present invention. The therapeutic device 10 generally comprises a temperature moderating system 200 (see FIG. 8), a heating/cooling system 300 (see FIG. 7), a compression system 400 (see FIG. 9), a control system 100 (see FIG. 10) housed within a container 20, a garment 30, and an umbilical cord 40.

The container 20 is preferably sized from 50 cu. in. up to and including 1000 cu. in. and preferably weighs from 2 lbs up to and including 20 lbs. The container 20 may be comprised of metal and/or synthetic material.

Figure 2:
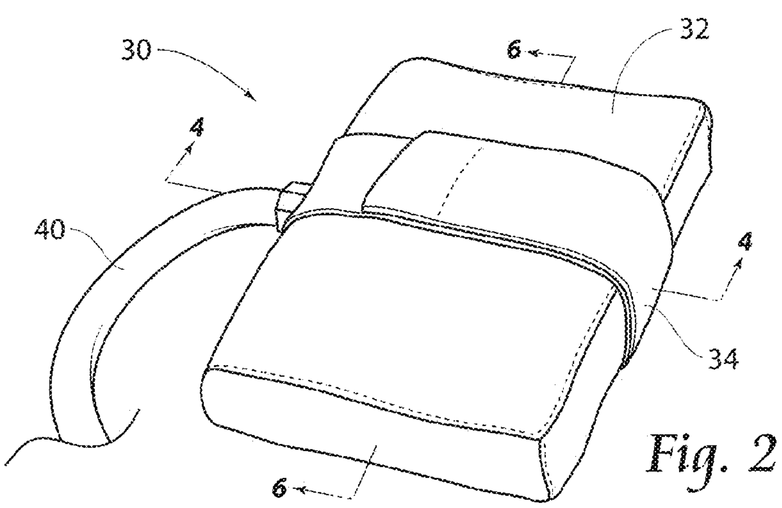
FIG. 2 is a perspective view of the garment shown in FIG. 1.
Figure 3:
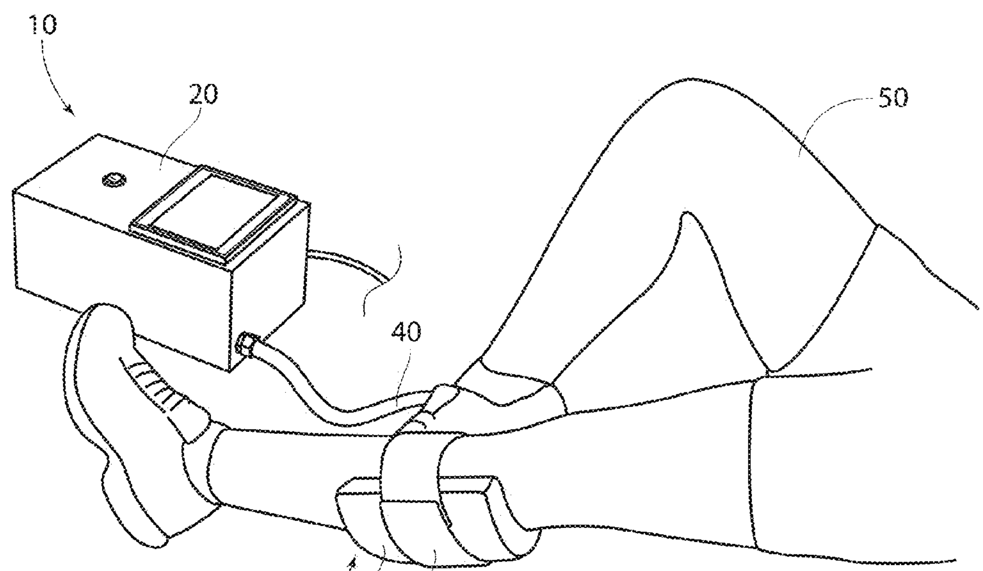
FIG. 3 is a perspective view of the treatment system in FIG. 1 applied to a patient.

FIG. 2 shows the garment 30 comprising an envelope 32 and a strap 34. FIG. 3 illustrates an embodiment of the garment 30 affixed to a patient 50 wherein the strap 34 secures the envelope 32 to the patient 50. It is contemplated that the garment 30 may be configured to accommodate patients of various sizes and be designed to fit to various parts of the patient 50 being treated (i.e., back, thigh, calf, knee, ankle, head, wrist, elbow, hand, forearm, shoulder, etc.). FIG. 3 further illustrates the garment 30 attached to the container 20 via the umbilical cord 40.

Figure 4:
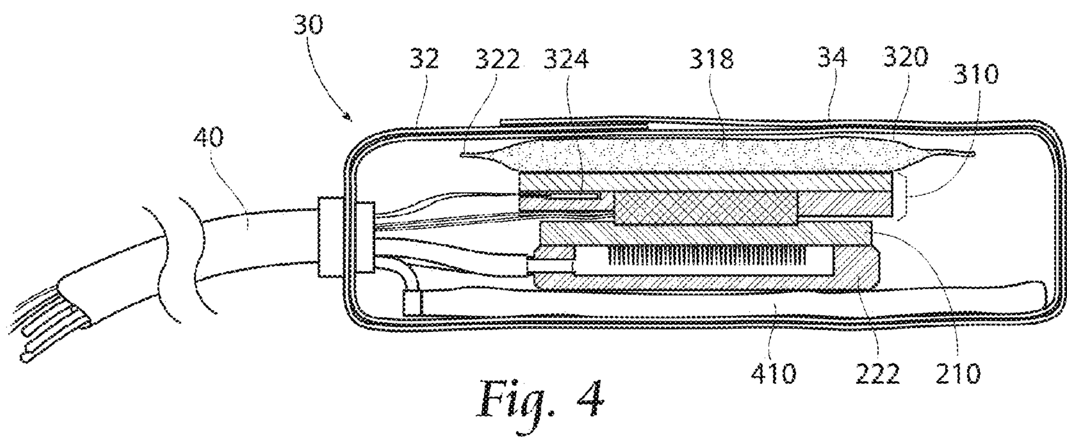
FIG. 4 is a cut-away view of the garment shown in FIG. 3 along line 4-4.

FIG. 4 shows a cut-away view of the inside of the envelope 32 of the garment 30 along line 4-4 of FIG. 2. Elements of the temperature moderating system 200 (FIG. 8) located within the envelope 32 include a heat sink 210 and a heat transfer apparatus housing 222. Elements of the heating/cooling system 300 (FIG. 7) located within the envelope 32 include a therapeutic delivery apparatus 310, a thermocouple 324, and a substrate 318. The compression system 400 (FIG. 9) includes an inflatable bladder 410 located within the envelope 32. These systems will be discussed in further detail below.

Figure 5:
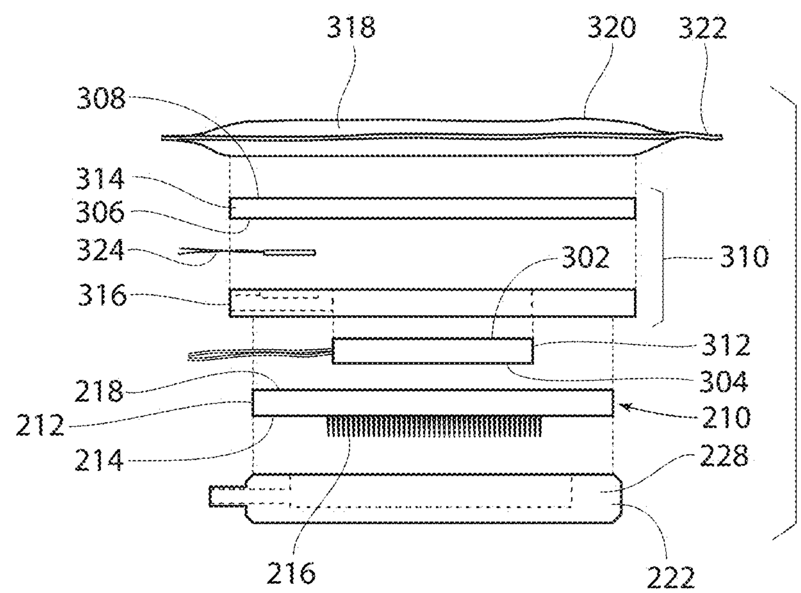
FIG. 5 is an exploded view of the internal components of the garment shown in FIG. 1.

FIG. 5 further illustrates in an exploded view the therapeutic delivery apparatus 310, which is comprised of a thermoelectric cooler/module (TEC/TEM) 312, a delivery head 314, and a retainer 316; the substrate 318; the thermocouple 324; the heat sink 210; and the heat transfer apparatus housing 222.

Figure 6:
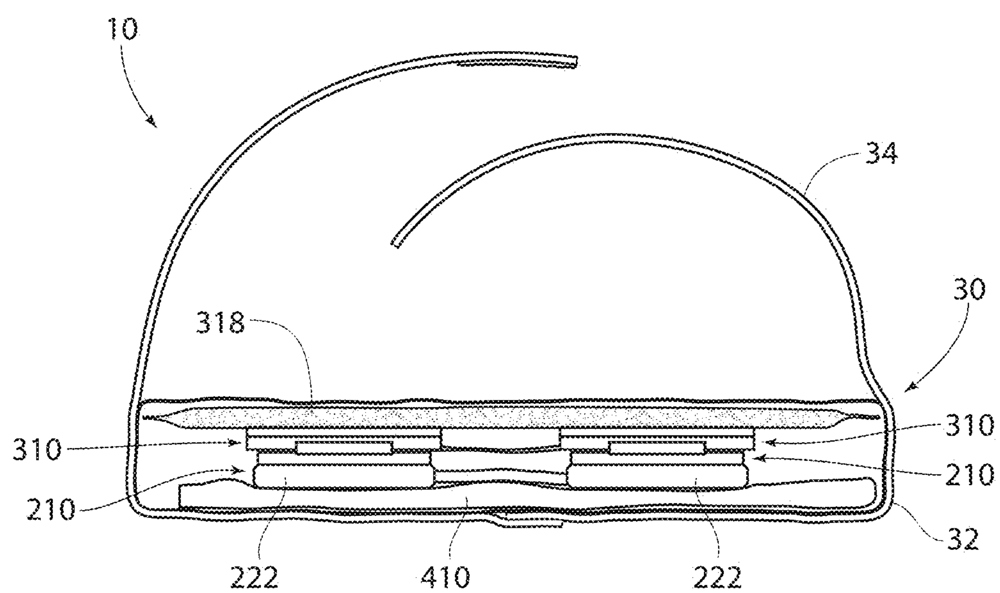
FIG. 6 is a cut-away view of the garment shown in FIG. 3 along line 6-6.

FIG. 6 provides a cut-away view of the garment 30 along line 6-6 of FIG. 2. As depicted here, within the garment 30 there is more than one therapeutic delivery apparatus 310, two heat sinks 210, and two heat transfer apparatus housings 222. The substrate 318 and the bladder 410 are shown shared between the therapeutic delivery apparatus 310, heat sinks 210, and heat transfer apparatus housings 222. As shown here, it is contemplated that one or more therapeutic heads 310 and the corresponding heat sinks 210 and heat transfer apparatus housings 222 may be placed within one garment envelope 32.

Additionally or alternatively, the garment 30 may comprise more than one envelope 32 whereby each envelope 32 comprises a predetermined capacity and shape configured to retain one or more of the combinations of the therapeutic delivery apparatus 310, heat sink 210, heat transfer apparatus housing 222 in an advantageous manner to deliver a more balanced and evenly distributed treatment depending on the size and location of the part of the patient body being treated.

Figures 7A, 7B:
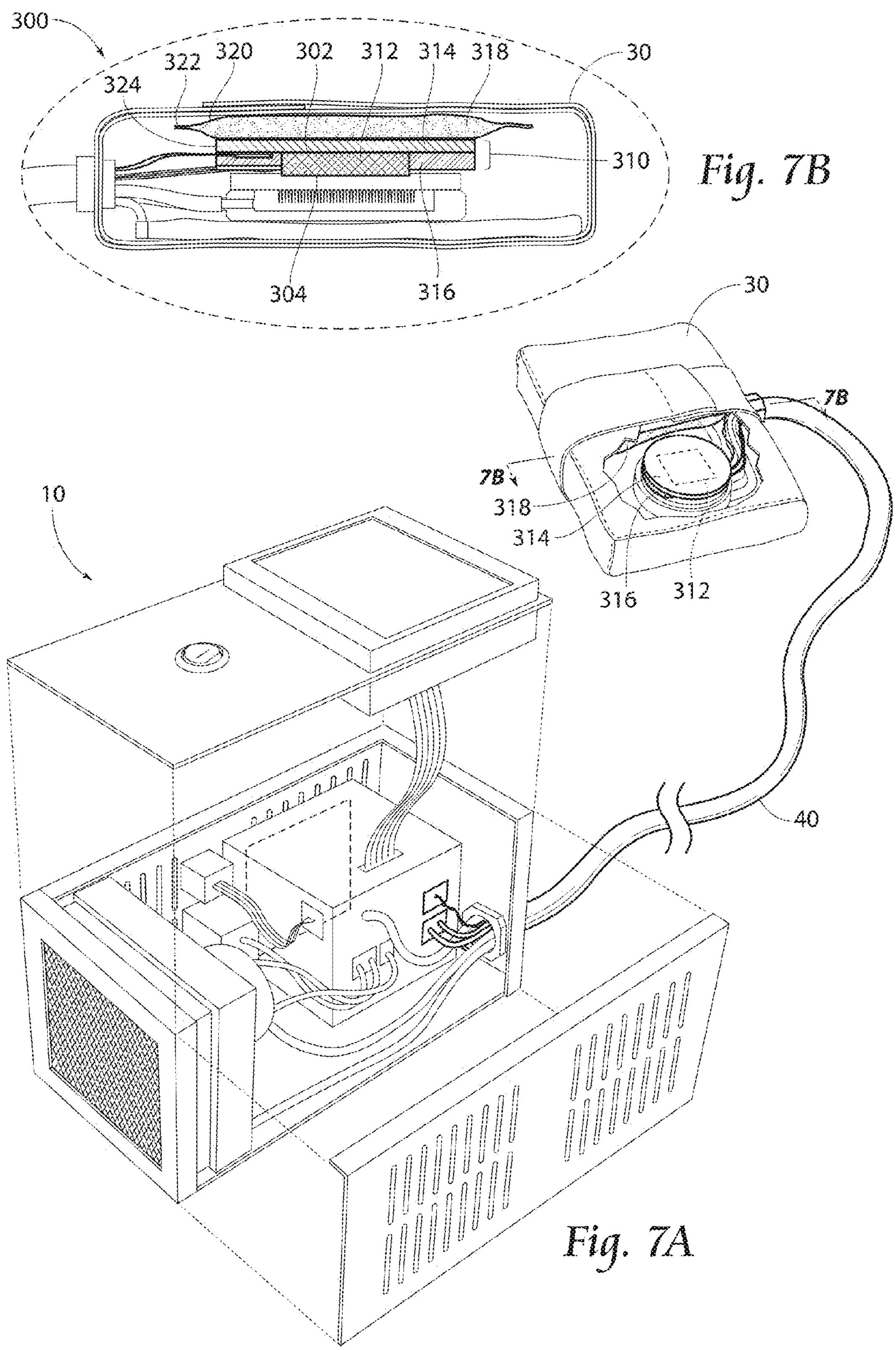
FIG. 7A is an exploded view of the container shown in FIG. 1, highlighting the heating/cooling system.
FIG. 7B is a cut-away view of the garment shown in FIG. 7A along line 7B-7B, highlighting the heating/cooling system.

Looking to FIGS. 7A and 7B, the elements of the heating/cooling system 300 are highlighted. As stated above, the heating/cooling system 300 preferably comprises the therapeutic delivery apparatus 310 comprised of the TEM 312, the delivery head 314, and the retainer 316; the substrate 318; and the thermocouple 324.

The TEM 312 may be a thermoelectric module as is known in the art and provides heating and cooling to a targeted area of the body (human or animal) by way of the Peltier effect. The TEM 312 has a delivery side 302 and a transfer side 304 and is electrical communication with the control system 100.

The delivery head 314 has a first surface 306 and a second surface 308 and is preferably comprised of copper, aluminum, steel, iron, brass, or other metal; a conductive synthetic material; or other conductive material. It is contemplated that the delivery head 310 may comprise one or more layers of the same material or a mixture of materials.

The substrate 318 preferably comprises a pouch 320 of heat transfer fluid/compound (hidden). The pouch 320 is preferably made from a flexible material such as, elastomer, a solid or flexible PVC, mylar, metalized plastic, rubber, urethane or polyethylene coated materials and other non-permeable materials.

The retainer 316 preferably maintains the positioning of the TEM 312 on the delivery head 314 and also provides spacing to reduce and/or displace any forces around the TEM 312 that may be experienced by the therapeutic delivery apparatus 310.

The heat transfer compound is contained within the pouch 320 by a heat seal 322 (shown here), a gasket, or a pressure fitting. As non-limiting examples, the heat transfer compound (hidden) may comprise thermal grease, natural or synthetic oils, gel, or other inorganic or organic chemicals in an aqueous or semi-solid form. The liquid and semi-solid mixtures may contain aluminum, copper, iron, and other metals in the form of powder, pellets, beads, and other configurations.

The thermocouple 324 is preferably placed in contact with at least one of the delivery head 314 and the substrate 318. The placement of the thermocouple 324 provides more accurate temperature data regarding the temperature of the heat or cold being applied to the body part at the application point, not remotely. The thermocouple 324 is preferably in electrical communication with the control system 100.

Figures 8A, 8B:
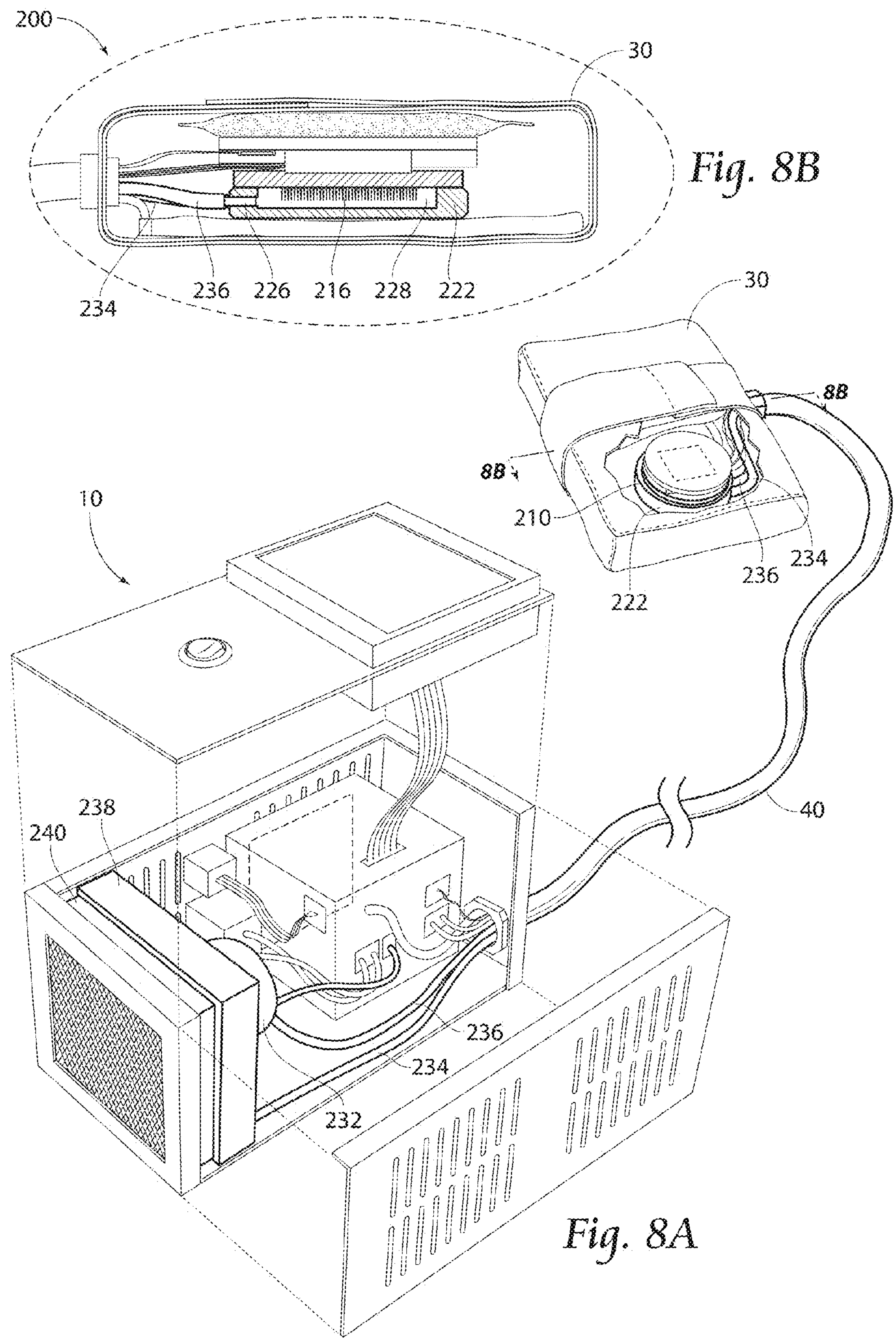
FIG. 8A is an exploded view of the container shown in FIG. 1, highlighting the temperature moderating system.
FIG. 8B is a cut-away view of the garment shown in FIG. 8A along line 8B-8B, highlighting the temperature moderating system.

The elements of the temperature moderating system 200 are highlighted in FIGS. 8A and 8B. The temperature moderating system 200 generally comprises the heat sink 210 and a heat transfer apparatus 220. In the embodiment shown, the heat transfer apparatus 220 comprises the housing 222, a fluid (not shown), a fluid pump 232, an input hose 234, and an output hose 236. The housing 222 comprises an input passage 224 (hidden), an output passage 226, and an opening 228. The fluid pump 232 is housed within the container 20 (see FIG. 1). The fluid pump 232 is in fluid communication with the input passage 224 and the output passage 226 via the input hose 234 and the output hose 236, respectively. It is contemplated that at least one of the input hose 234 and the output hose 236 is connected to a radiator 238 (shown in FIG. 3) and a fan unit 240 is preferably provided with the radiator 238.

Looking back, FIG. 5 illustrates the heat sink 210 in greater deal. The heat sink 210 comprises a plate 212 with a first side 214, a second side 218, and fins 216 extending substantially perpendicularly from the first side 214. Preferably, the fins 216 are received within the opening 228 in the housing 222 and a liquid tight connection is made between the housing 222 and the plate 212 whereby the second side 218 of the plate 212 is exposed.

The delivery side 302 of the TEM 312 is preferably adhered in flush contact to the first surface 306 of the delivery head 314, and the transfer side 304 of the TEM 312 is preferably adhered to the second side 218 of the heat sink plate 212. The TEM 312 may additionally or alternatively be secured to the delivery head 314 and the heat sink plate 212 by mechanical fasteners or magnets (not shown).

The second surface 308 of the delivery head 314 is preferably placed directly against the substrate 318. The delivery head 314 and the substrate 318 transfer the heat or cold from the TEM 312 to the area being treated. The substrate pouch 320 provides an even transfer and application of heat or cold from the TEM 312 as it more easily forms to the body part on which it is placed. The thermal energy transfer characteristics and placement of the TEM 312 and the substrate 318 will enhance penetration of the heat or cold and improve the control of the device 10 and allows the device 10 to maintain close temperature tolerances.

Heat produced by the TEM 312 during a cooling cycle and cold produced by the TEM 312 during a heating cycle may be moderated by the temperature moderating system 200. Fluid (not shown) is preferably pumped by the fluid pump 232 through the input hose 234, into the housing 222 through the input passage 224, over and through the heat sink fins 216, out of the housing 222 through the output passage 226, and back to the pump 232 and/or the radiator 238. Additionally or alternatively, the heat transfer apparatus may comprise the housing 222 with a fan (not shown) to provide cooling.

As the heat or cold provided by the TEM 312 is directly transferred from the TEM 312 through the delivery head 314 and the substrate 318 to the body part (see FIG. 3), the device 10 does not require circulating chilled or heated liquids to directly cool or heat the body tissue. Other known devices use chilled or heated liquids transported through tubing from the main unit to the "garment" attached to the body. This type of construction limits the effectiveness of the treatment, since thermal energy from the environment tends to warm chilled liquids, or cool heated liquids, on their journey from the main unit to the treated area. This described execution, on the other hand, puts the TEM 312 in close proximity to the treated area and transfers the cold or heat directly to the area of the body being treated, thus more efficiently providing the thermal treatment needed.

Figures 9A, 9B:
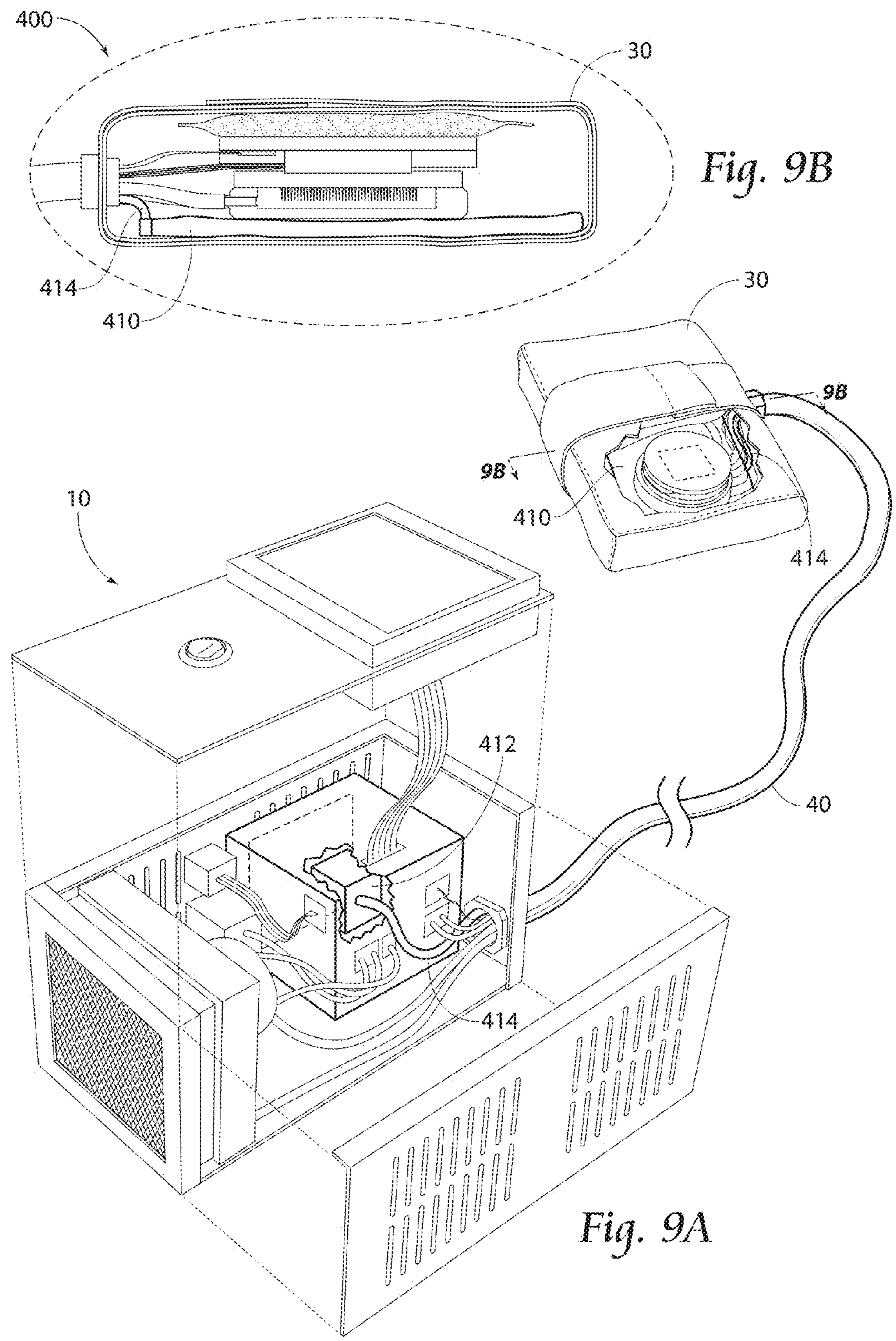
FIG. 9A is an exploded view of the container shown in FIG. 1, highlighting the compression system.
FIG. 9B is a cut-away view of the garment shown in FIG. 9A along line 9B-9B, highlighting the compression system.

The compression system 400 is shown highlighted in FIGS. 9A and 9B. The compression system 400 preferably comprises an inflatable bladder 410, an air pump 412, and airway tubing 414. The bladder 410 is connected to the air pump 412 by the airway tubing 414.

The garment 30 is preferably configured to removably contain the inflatable bladder 410, the therapeutic delivery apparatus 310, the heat sink 210, and the heat transfer housing 222, as discussed above and illustrated in the figures.

Figure 10:
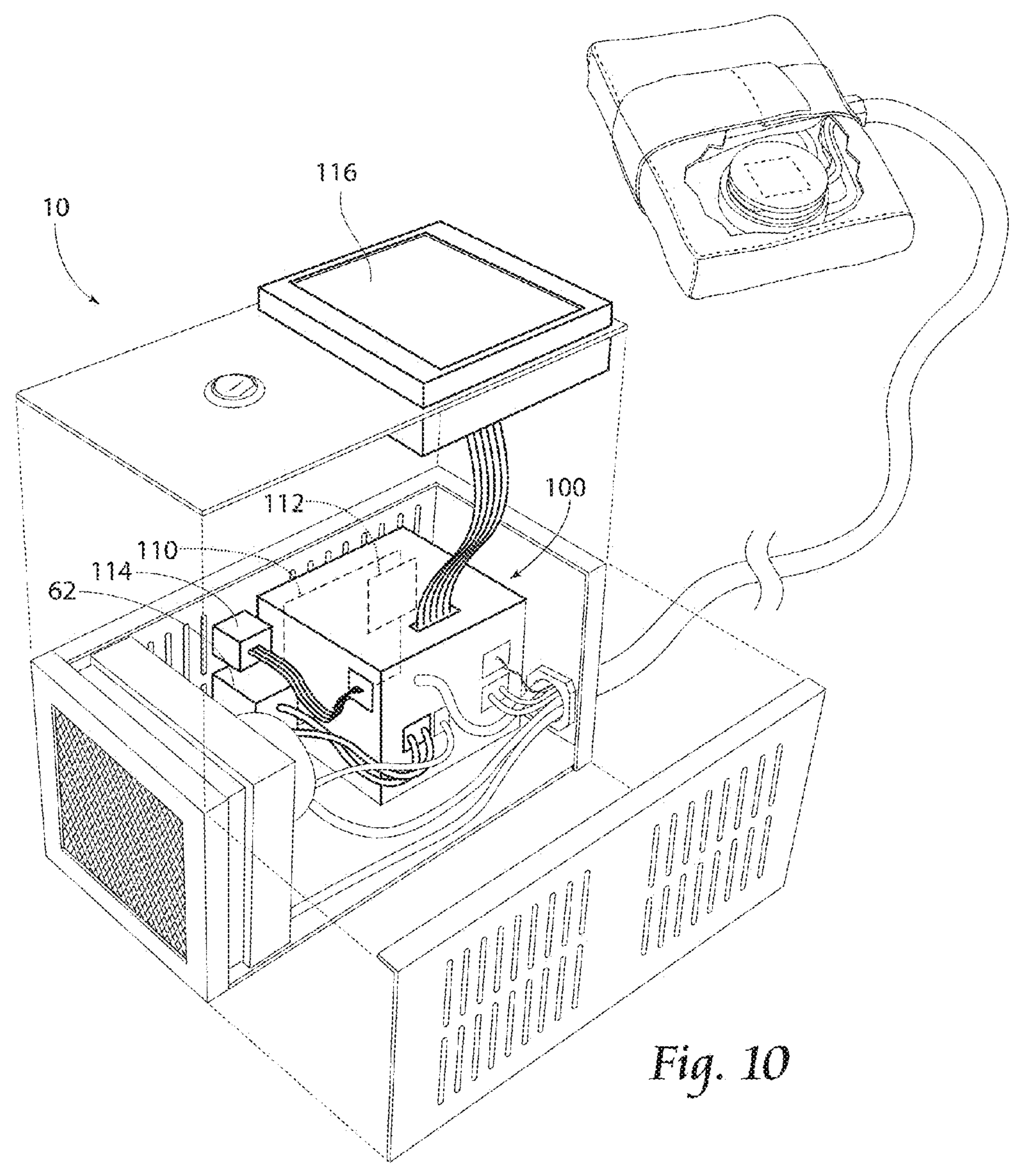
FIG. 10 is an exploded view of the container shown in FIG. 1, highlighting the control system.

Looking to FIG. 10, the control system 100 is shown. The control system 100 preferably comprises a circuit board 110 with a microprocessor 112; a touch-screen interface 116; and a USB port 114 or similar data access point.

Preferably, the umbilical cord 40 houses the heat transfer apparatus hoses 234,236, airway tubing 414, and wiring 60 to provide electrical communication between the control system 100, the TEM 312, and the thermocouple 324.

The device 10 is preferably energized by at least one of a battery, a connection to a 120V AC electrical outlet, and a connection to 12V DC power outlet. FIG. 1 illustrates a cord-and-plug 60 to plug into a standard 120V AC electrical outlet (not shown) and FIG. 10 shows a transformer 62 to step down the incoming voltage.

Figure 11:
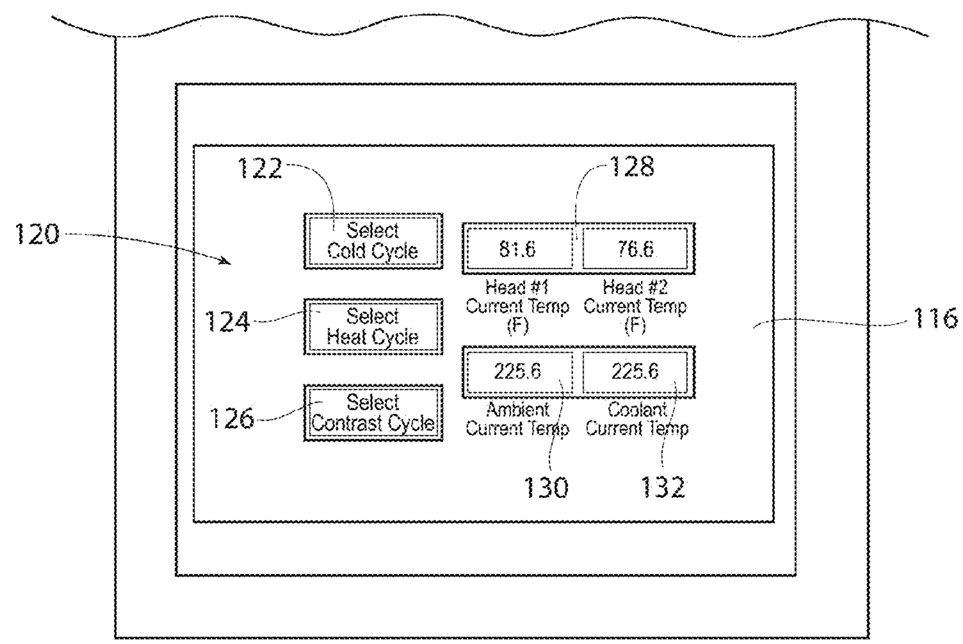
FIG. 11 is a first top view of the therapeutic device display shown in FIG. 1, according to the present invention.

Looking to FIG. 11, a first display 120 is shown on the touch-screen interface 116. The first display 120 preferably provides the option to select a cold cycle 122, a heat cycle 124, or a cycle which contrasts between a cold cycle and a heat cycle 126. The first display 120 also provides the current temperature 128 of the therapeutic delivery apparatus 310 (FIG. 7), the current ambient air temperature 130, and the current cooling fluid temperature 132.

Figure 12:
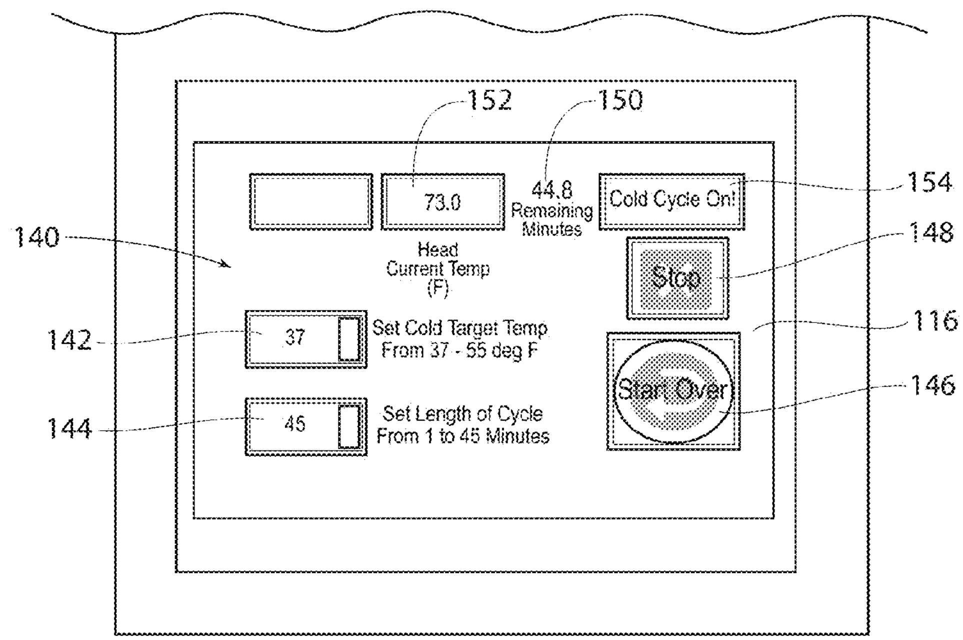
FIG. 12 is a second top view of the therapeutic device display shown in FIG. 1, according to the present invention.

FIG. 12 shows an example of a second display 140 when the cold cycle option 122 (FIG. 11) from the first display 120 is selected. Here, the target cold temperature 142 and the cycle length 144 may be set; the therapy can be started/started over 146, and stopped 148. The second display 140 may provide current operating statuses, for example, the therapy time remaining 150, the current temperature 152 of the therapeutic delivery apparatus 310 (see FIG. 7), and the state of therapy 154 (i.e., on or off).

The device 10 preferably provides a heath care professional with the ability to set a sequence of time, temperature, pressure, cycles, Transcutaneous Electrical Nerve Stimulation (TENS), and/or massage via the touch-screen interface 116 to promote the best analgesic or therapeutic result. The device 10 may be operated for at least one treatment session comprising at least one temperature cycle and at least one pressure cycle. For instance the temperature cycle may apply a first temperature for a first temperature duration, a second temperature for a second temperature duration, and a third temperature for a third temperature duration, and the pressure cycle may apply a first pressure for a first pressure duration and a second pressure for a second pressure duration, whereby the temperature cycle and the pressure cycle occur contemporaneously. It should be understood to those having skill in the art that any number of cycles and degrees of temperatures, pressures, and other therapeutic stimuli may be applied to a patient contemporaneously according to the present invention are contemplated herein.

As a non-limiting example, a temperature cycle may comprise the application of a first temperature of 35° F. for a first temperature duration of 20 minutes and then a second temperature of 50° F. for a second temperature duration of 20 minutes, and during the 40 minute temperature cycle a 10 minute pressure cycle comprising the application of a first pressure of 100 mmHg applied for a first pressure duration of 2 minutes and then a second pressure of 75 mmHg for 8 minutes is repeated.

Additionally or alternatively, a treatment program may be selected from a plurality of pre-installed programs pertaining to the various forms of stimuli and treatments mentioned above. Programs may also be customized or custom-made to fit a certain patient's treatment requirements.

The device 10 may be configured to selectively prohibit patient access to the controls in order to provide complete control by the professional health care provider.

The device 10 may be configured to be accessed remotely and/or wirelessly to provide program updates, treatment review, and/or modification of the regimen as appropriate. Additionally or alternatively, the use history and operation of the device 10 may be maintained for professional management and review, available to view on the touch-screen interface 116, output to a printer (not shown), or accessed by other devices (not shown). For example, the control system 100 and the touch-screen interface 116 may link with Smartphone Applications ("apps") for delivery and communication of information and settings used with the device 10, including notification of completion of a treatment session and other measurable data.

The ability to monitor the prescribed treatments either in-time or over an extended period of time will provide valuable data with respect to if a patient is following the treatment schedule, how the patient is progressing with the treatment compared to the forecasted progress. Ultimately, this data may be used to alter treatment sessions and speed recovery.

The controllable temperature range is preferably from about 10° F. up to and including 150° F. The controllable pressure range is preferably from about 0 mmHg up to and including 1000 mmHg and an air flow range from about 5 l/min up to and including 50 l/min.

The form of applied pressure is selectable between constant, intermittent, and sequential. As a non-limiting example, the device 10 may provide 5 minutes of pressure at 200 mm Hg followed by 5 minutes of pressure at 0 mm Hg in one cycle; however, any number of combinations of time and pressure are contemplated.

The device 10 is preferably configured to change between applying heat and applying cold by reversing the polarity of the voltage applied to the TEM 312. The rate of temperature change may be controllable through an installed program or user input.

The foregoing is considered as illustrative only of the principles of the invention. Furthermore, because numerous modifications and changes will readily occur to those skilled in the art, it is not desired to limit the invention to the exact construction and operation shown and described. Provided that a compression device that allows for the delivery of thermal energy and cryotherapy to provide heating and cooling as described herein, such a device should be considered as falling within the scope of the present invention. While the preferred embodiment has been described, the detail may be changed without departing from the invention, which is defined by the claims.

We claim:

1. A therapeutic thermal compression device comprising:

a heating/cooling system comprising a thermoelectric module (TEM) having a delivery side and a transfer side and configured to operate in at least one of a heating cycle and a cooling cycle;

a temperature moderating system configured to remove heat from the transfer side of the TEM by circulating a fluid over a heat sink attached to the transfer side of the TEM when the TEM is operating in the cooling cycle;

a compression system comprising an inflatable bladder adjacent to the TEM; and a control system configured to coordinate the operation of the temperature moderating system and the compression system, wherein the heating/cooling system further comprises a delivery head having a first surface in thermal communication with the delivery side of the TEM, wherein the delivery head further comprises a second surface opposite the first surface and the heating/cooling system further comprises a substrate in thermal communication with the second surface of the delivery head, and wherein the substrate is a sealed pouch of thermal grease.

2. A therapeutic thermal compression device comprising:

a thermoelectric module (TEM) with a delivery side and a transfer side;

a thermocouple in thermal communication with the TEM;

a heat sink having a first side with a plurality of fins extending therefrom and a second side;

the second side of the heat sink affixed to the transfer side of the TEM;

a housing having an opening and an input passage and an output passage;

the first side and the plurality of fins of the heat sink received within the opening of the housing;

a fluid;

a radiator in fluid communication with the housing through an input hose attached to the input passage of the housing and an output hose attached to the output passage of the housing;

the pump configured to pump the fluid between and through the radiator, the first hose, the second hose, and the housing; and a control system in electrical communication with the TEM, the thermocouple, and the pump, the therapeutic thermal compression device further comprising a delivery head having a first surface in thermal communication with the delivery side of the TEM, a substrate and wherein the delivery head further comprises a second surface opposite the first surface, whereby the substrate is in thermal communication with the second surface of the delivery head, and wherein the substrate is a sealed pouch of thermal grease.

* * * * *